(12) United States Patent
Christensen

(10) Patent No.: US 6,929,665 B2
(45) Date of Patent: Aug. 16, 2005

(54) PROSTHETIC FOOT WITH A RESILIENT ANKLE

(75) Inventor: Roland J. Christensen, 192 E. 100 North, Fayette, UT (US) 84630

(73) Assignee: Roland J. Christensen, Fayette, UT (US)

( * ) Notice: Subject to any disclaimer, the term of this patent is extended or adjusted under 35 U.S.C. 154(b) by 0 days.

(21) Appl. No.: 10/268,014

(22) Filed: Oct. 8, 2002

(65) Prior Publication Data
US 2004/0068327 A1 Apr. 8, 2004

(51) Int. Cl.$^7$ .................................................. A61F 2/66
(52) U.S. Cl. ........................................... 623/52; 623/55
(58) Field of Search ............................. 623/47, 50, 52, 623/53, 55, 56

(56) References Cited

U.S. PATENT DOCUMENTS

| | | |
|---|---|---|
| 42,799 A | 5/1864 | Shepard |
| 92,031 A | 6/1869 | Foster |
| 292,800 A | 2/1884 | Furrer |
| 497,026 A | 5/1893 | Judson |
| 1,001,641 A | 8/1911 | Harrison |
| 1,191,633 A | 5/1916 | Waggott |
| 1,996,874 A | 4/1935 | Mascau |
| 2,036,830 A | 4/1936 | Rowley |
| 2,379,538 A | 7/1945 | Meierhofer |
| 2,443,356 A | 6/1948 | Mathis |
| 2,453,969 A | 11/1948 | Carter |
| 2,470,480 A | 5/1949 | Fogg |
| 2,570,735 A | 10/1951 | Weise |
| 2,617,115 A | 11/1952 | Ellery |
| 2,640,200 A | 6/1953 | Wisburn |
| 2,843,853 A | 6/1958 | Mauch |
| 3,551,914 A | 1/1971 | Woodall |
| 3,871,032 A | 3/1975 | Karas |

(Continued)

FOREIGN PATENT DOCUMENTS

| | | | |
|---|---|---|---|
| BR | 9304552-2 A | * 7/1995 | ............. A61F/2/60 |
| RU | 2033772 | 4/1995 | |
| SU | 560606 | 7/1977 | |

Primary Examiner—David H. Willse
(74) Attorney, Agent, or Firm—Thorpe North & Western

(57) ABSTRACT

A prosthetic foot device includes an elongated upper forefoot portion, an ankle portion, and a lower footplate. The forefoot portion can extend rearwardly through an upper attachment section, downwardly through an ankle section, forwardly through an arch section, and to a toe section. The ankle portion can attach to the forefoot portion, and can extend rearwardly through an upper attachment section, downwardly through an ankle section, forwardly under the ankle section of the forefoot portion, and rearwardly to a heel section, in a substantial s-shaped profile. The lower footplate can attach to the ankle or forefoot portion, and can extend through a heel section, an arch section, and to a toe section. The upper forefoot, the ankle portion, and the lower footplate each being flexible to store energy and resilient to return energy.

17 Claims, 3 Drawing Sheets

U.S. PATENT DOCUMENTS

| | | | |
|---|---|---|---|
| 3,906,552 A | 9/1975 | Weber | |
| 3,920,610 A | 11/1975 | Wagner | |
| 3,956,775 A | 5/1976 | Moore | |
| 3,982,280 A | 9/1976 | Asbelle et al. | |
| 4,089,072 A | 5/1978 | Glabiszewski | |
| 4,328,594 A | 5/1982 | Campbell et al. | |
| 4,506,395 A | 3/1985 | Haupt | |
| 4,547,913 A | 10/1985 | Phillips | |
| 4,645,509 A | 2/1987 | Poggi et al. | |
| 4,676,801 A | 6/1987 | Lundeen | |
| 4,721,510 A | 1/1988 | Cooper et al. | |
| 4,822,363 A | 4/1989 | Phillips | |
| 4,865,611 A | 9/1989 | Al-Turaiki | |
| 4,938,775 A | 7/1990 | Morgan | |
| 4,959,073 A | 9/1990 | Merlette | |
| 5,019,109 A | 5/1991 | Voisin | |
| 5,030,239 A | 7/1991 | Copes | |
| 5,037,444 A | 8/1991 | Phillips | |
| 5,112,356 A | 5/1992 | Harris et al. | |
| 5,116,383 A | 5/1992 | Shorter et al. | |
| 5,116,384 A | 5/1992 | Wilson et al. | |
| 5,181,932 A | 1/1993 | Phillips | |
| 5,181,933 A | 1/1993 | Phillips | |
| 5,217,500 A | 6/1993 | Phillips | |
| 5,258,039 A * | 11/1993 | Goh et al. | 623/55 |
| 5,290,319 A | 3/1994 | Phillips | |
| 5,376,133 A | 12/1994 | Gramnas | |
| 5,376,141 A | 12/1994 | Phillips | |
| 5,387,246 A | 2/1995 | Phillips | |
| 5,425,781 A | 6/1995 | Allard et al. | |
| 5,425,782 A | 6/1995 | Phillips | |
| 5,443,528 A | 8/1995 | Allen | |
| 5,443,529 A | 8/1995 | Phillips | |
| 5,458,656 A | 10/1995 | Phillips | |
| 5,464,441 A | 11/1995 | Phillips | |
| 5,482,513 A | 1/1996 | Wilson | |
| 5,486,209 A | 1/1996 | Phillips | |
| 5,507,838 A | 4/1996 | Chen | |
| 5,509,936 A | 4/1996 | Rappoport et al. | |
| 5,509,938 A | 4/1996 | Phillips | |
| 5,514,185 A | 5/1996 | Phillips | |
| 5,514,186 A | 5/1996 | Phillips | |
| 5,549,714 A | 8/1996 | Phillips | |
| 5,571,210 A | 11/1996 | Lindh | |
| 5,571,213 A | 11/1996 | Allen | |
| 5,593,455 A | 1/1997 | Phillips | |
| 5,593,456 A | 1/1997 | Merlette | |
| 5,593,457 A | 1/1997 | Phillips | |
| 5,653,767 A | 8/1997 | Allen et al. | |
| 5,653,768 A * | 8/1997 | Kania | 623/55 |
| 5,725,598 A | 3/1998 | Phillips | |
| 5,728,175 A | 3/1998 | Rincoe | |
| 5,728,176 A | 3/1998 | Phillips | |
| 5,728,177 A | 3/1998 | Phillips | |
| 5,766,265 A | 6/1998 | Phillips | |
| 5,769,896 A | 6/1998 | Rosendahl et al. | |
| 5,776,205 A | 7/1998 | Phillips | |
| 5,779,735 A | 7/1998 | Molino | |
| 5,800,565 A | 9/1998 | Biedermann | |
| 5,800,569 A | 9/1998 | Phillips | |
| 5,824,112 A | 10/1998 | Phillips | |
| 5,888,238 A | 3/1999 | Phillips et al. | |
| 5,893,891 A | 4/1999 | Zahedi | |
| 5,899,944 A | 5/1999 | Phillips | |
| 5,976,191 A | 11/1999 | Phillips | |
| 5,993,488 A | 11/1999 | Phillips | |
| 6,019,795 A | 2/2000 | Phillips | |
| 6,071,313 A | 6/2000 | Phillips | |
| 6,165,227 A | 12/2000 | Phillips | |
| 6,206,934 B1 | 3/2001 | Phillips | |
| 6,254,643 B1 | 7/2001 | Phillips | |
| 6,261,324 B1 | 7/2001 | Merlette | |
| 6,280,479 B1 | 8/2001 | Phillips | |
| 6,290,730 B1 | 9/2001 | Pitkin et al. | |
| 6,602,295 B1 * | 8/2003 | Doddroe et al. | 623/55 |

\* cited by examiner

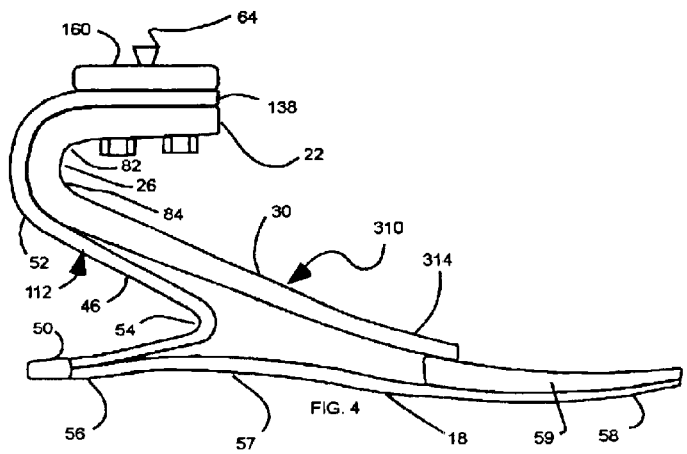
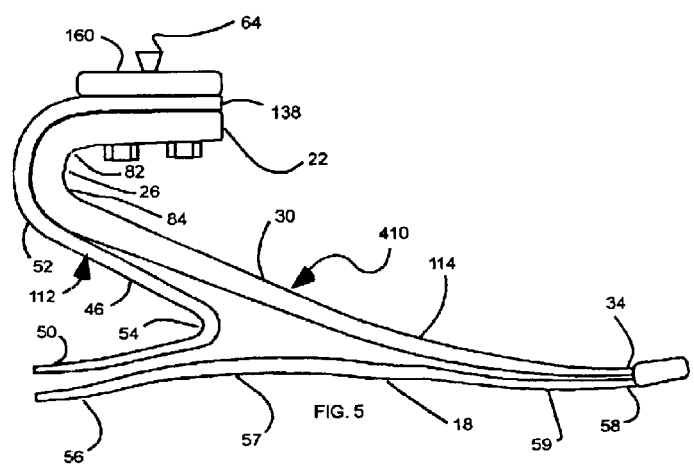
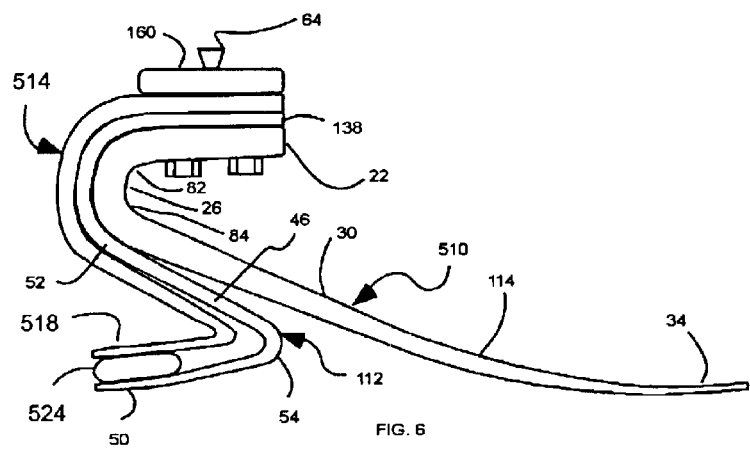

PROSTHETIC FOOT WITH A RESILIENT ANKLE

BACKGROUND OF THE INVENTION

1. Field of the Invention

The present invention relates generally to prosthetic feet. More particularly, the present invention relates to a prosthetic foot with a resilient ankle.

2. Related Art

Many individuals have lost a limb for various reasons including war, accident, or disease. In most instances these individuals are not only able to live relatively normal lives, but physically active lives as well. Often times, these individuals are aided in their everyday lives by a prosthetic limb. The objective of prosthesis is to provide an artificial limb that simulates the function and natural feel of the replaced limb.

With respect to prosthetic feet, the development of a functional and natural artificial foot has been limited only by material and imagination. Many designs have attempted to copy the anatomy of the foot or simulate its actions by replacing the bones and muscle with various mechanical components. Other designs have departed radically from mere anatomical copying or mechanical simulation by replacing the entire foot with an energy storage element, such as a spring. As the user steps onto the foot, the user's weight compresses the spring. As the user moves forward, the user's weight comes off the foot and the energy stored in the spring is used to propel the user forward.

In addition, the performance of these energy storing feet has been altered in various ways, such as by using multiple springs in various configurations, using bladders or resilient materials disposed between various elements, and using multiple springs that deflect at different intervals of foot deflection to add resistance.

As described above, such energy-storing prosthetic feet typically have either a J-shape or a C-shape configuration or profile. The J-shape feet have a vertical attachment section, while the C-shaped feet have a horizontal attachment section. While the vertical attachment section of the J-shape feet can be relatively long, depending on the length of the residual limb of the amputee, the horizontal attachment section of the C-shape feet tend to be relatively short, due to the constraint of having the prosthetic foot contained in a general outline of a natural foot. It will be appreciated that the shape and dimensions of the foot can affect or limit the performance or bending characteristics of the foot.

SUMMARY OF THE INVENTION

The continued development of improved prosthetic feet is an ongoing goal. It has been recognized that it would be advantageous to develop a prosthetic foot with improved shock absorption or a softer heel.

The invention provides a prosthetic foot device with an elongated ankle portion to provide shock absorption or cushioning during use. The foot device can include the ankle portion attached to, and supporting, an elongated forefoot portion. The forefoot portion can extend 1) rearwardly through an upper attachment section, 2) downwardly through an ankle section, 3) forwardly through an arch section, and 4) to a toe section. The ankle portion can extend 1) rearwardly through an upper attachment section, 2) downwardly through an ankle section 3) forwardly under the ankle section of the forefoot portion, and 4) rearwardly to a heel section. The forefoot portion and the ankle portion can be flexible to store energy and resilient to return energy. Thus, the ankle section can have a substantial s-shaped profile. The configuration of the ankle section provides vertical shock absorption or cushioning to the amputee. The attachment section of the upper forefoot and the attachment section of the ankle portion can be attached to one another, and coupled to the stump of the amputee.

In accordance with a more detailed aspect of the present invention, the forefoot portion and the ankle portion can include a composite material with fiber in a resin matrix.

In accordance with another more detailed aspect of the present invention, the foot device can further conclude a lower footplate attached to the ankle portion. The footplate can include a heel section attached to the heel section of the ankle portion, and can extend forwardly to a toe section positioned at a toe, location of a natural foot.

In accordance with another more detailed aspect of the present invention, the foot device can further conclude a lower footplate attached to the forefoot portion. The footplate can include a toe section attached to the toe section of the forefoot portion, and can extend rearwardly to a heel section positioned at a heel location of a natural foot.

In accordance with another more detailed aspect of the present invention, the upper attachment section of the upper forefoot portion and the upper attachment section of the ankle portion are disposed at an oblique angle. The upper attachment section can be coupled to an attachment member having a lower oblique surface.

In accordance with another more detailed aspect of the present invention, the ankle section of the forefoot portion can include a discrete, straight section oriented substantially vertically. A first curved section can interconnect the attachment section and the straight section, and a second curved section can interconnect the straight section and the arch section. The discrete, straight ankle section with curved sections on both sides allow extra length to store and return energy during use, contribute to extra spring or cushion of the foot, and improve vertical shock resistance.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

FIG. 4 is a side view of a prosthetic foot in accordance with an embodiment of the present invention;

FIG. 5 is a side view of a prosthetic foot in accordance with an embodiment of the present invention; and FIG. 6 is a side view of a prosthetic foot in accordance with an embodiment of the present invention.

DETAILED DESCRIPTION

Figure 1A:
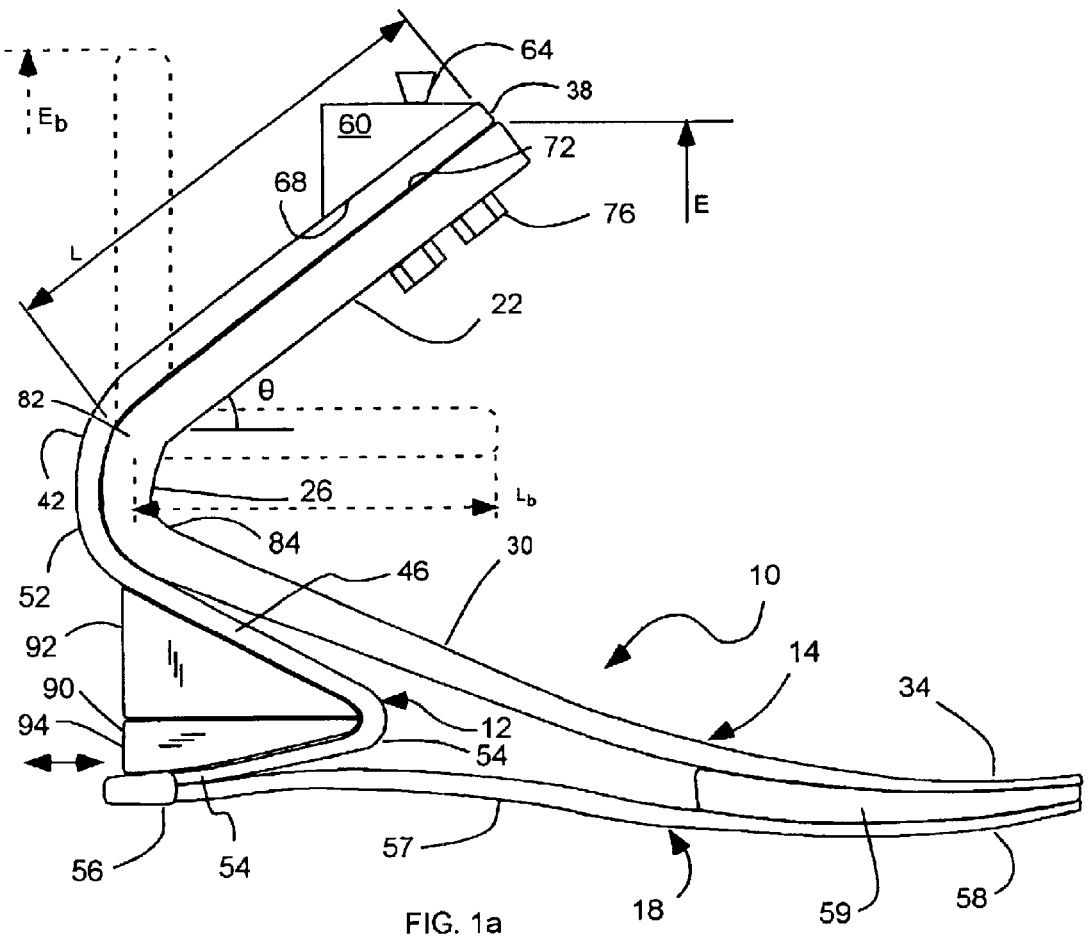
FIG. 1*a* is a side view of a prosthetic foot in accordance with an embodiment of the present invention.
Figure 1B:
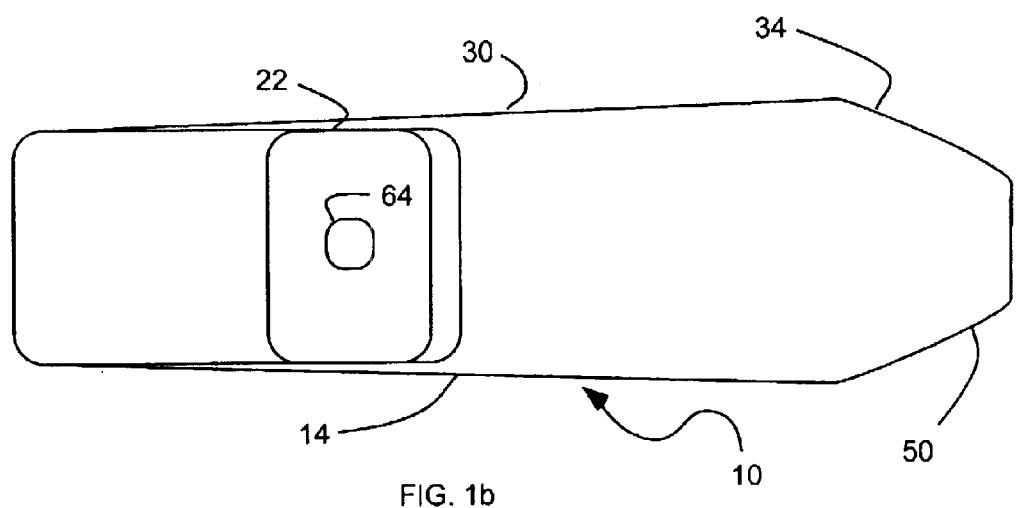
FIG. 1*b* is a top view of the prosthetic foot of FIG. 1*a;*

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

As illustrated in FIGS. 1a and b, a prosthetic foot, indicated generally at 10, in accordance with the present invention is shown with an elongated rear ankle portion 12 for absorbing shock and cushioning a limb or stump of an amputee. The prosthetic foot 10 can include an elongated, upper forefoot portion or forefoot 14. The forefoot portion 14 can include an upper attachment section 22 to be coupled to the limb or stump of the amputee. The forefoot portion 14 can extend rearwardly and downwardly through the attachment section 22, downwardly through an ankle section 26, forwardly and downwardly through an arch section 30, and forwardly to a toe section 34. The ankle section 26 is positioned at an ankle location of a natural foot. Likewise, the toe section 34 is positioned at a toe location of a natural foot. The toe location is a region near the forward end of the foot where toes of a natural foot would be located.

The forefoot portion 14 or ankle section 26 can be substantially arcuate. The arc formed by the ankle section can be smoothly curved, or can be formed of both straight and curved sections. The forefoot portion 14 or ankle 26 forms a vertically oriented arc extending between the attachment section 22 and the arch or toe sections. Thus, the forefoot portion or ankle section can form a curvilinear spring portion.

The ankle portion 12 includes an upper attachment section 38 attached to the attachment section 22 of the forefoot portion 14. The ankle portion 12 advantageously forms a resilient spring member to absorb shock and cushion the forefoot portion 14, and the stump or limb of the amputee. The ankle portion 12 extends rearwardly and downwardly through the attachment section 38, downwardly through an ankle section 42, forwardly and downwardly through an intermediate section 46 under the ankle section 26 of the forefoot portion 14, and rearwardly and downwardly through a heel section 50. The heel section 50 is positioned at a heel location of a natural heel. Thus, the ankle portion 12 can have a generally or substantially s-shaped profile. The attachment section 38 and the ankle section 42 of the ankle portion 12 can match and abut to the attachment section 22 and ankle section 26 of the forefoot portion 14.

The attachment section 38, the intermediate section 46, and the heel section 50 can be relatively straight or linear, and can extend forwardly and rearwardly, or in a posterior and anterior direction. Curved or angled sections are formed between the straight sections. A first or upper curved section 52 is formed between the attachment section 38 and the intermediate section 46, while a second or lower curved section 54 is formed between the intermediate section 46 and the heel section 50. The ankle portion 12 bends or flexes during use to cushion the foot device and to provide vertical shock absorption. Thus, the heel section 50 can displace towards the ankle section 26 of the forefoot portion 14 when a load or force is applied during use. Similarly, the intermediate section 46 can displace towards the ankle section 26 of the forefoot portion 14. Thus, the ankle portion 12 forms a resilient spring that can compress to absorb shocks and provide a cushion during use. The straight sections provide multiple spring elements.

The prosthetic foot 10 also can include a lower footplate 18 disposed under the forefoot portion 12 and ankle portion 14, and can extend a length of the foot from the heel to the toe. The lower footplate 18 can be attached to the rear ankle portion 12. The lower footplate 18 can include a heel section 56 attached to the heel section 50 of the ankle portion 12. The attachment of the lower footplate 18 to the ankle portion 12 can form the primary or only attachment of the footplate 18 to the prosthetic foot 10. The attachment can be formed by wrapping the heel sections 50 and 56 with fibers in a resin matrix. The lower footplate 18 can extend forwardly through the heel section 56, through an arch section 57, and to a toe section 58. The heel section 56 is disposed at a heel location of a natural foot. Likewise, toe section 58 is positioned at a toe location of a natural foot. A gap can be formed between the toe section 58 of the lower footplate 18 and the toe section 34 of the upper forefoot 14 so that the toe sections 34 and 58 are not positively or directly attached. A cushion member 59 can be disposed between the toe sections 34 and 58. The cushion member 59 can be formed of a flexible material that can compress as the toe section 58 of the lower footplate 18 moves towards the toe section 34 of the upper forefoot 14.

The foot 10 also can include an attachment member 60 to attach the upper forefoot portion 14 to a socket configured for the specific needs of the amputee. Such sockets typically have a portion adapted for standard attachment. The attachment member 60 can include a pyramid connector 64 on a top end or upper surface, as is well known in the art to connect to a socket on the stump of the amputee. The attachment sections 22 and 38 of the forefoot and ankle portions 14 and 12 can be coupled to the attachment member 60 by fasteners, such as bolts 76. For example, the bolts 76 can extend through apertures in the attachment sections 22 and 38 of the forefoot and ankle portions 14 and 12, and into threaded bores in the attachment member 60. It is of course understood that any type of fastener or connection can be used, including for example, screws, clips, etc.

The prosthetic foot 10 can include an oblique attachment, or an attachment forming an oblique angle. The attachment sections 22 and 38 can be oblique, or can be disposed at an oblique angle. In addition, the attachment member 60 can include a lower oblique surface 68. The attachment sections 22 and 38 of the forefoot and ankle portions 14 and 12 can include an upper oblique surface 72 that matches and attaches to the lower oblique surface 68.

The attachment sections 22 and 38 of the forefoot and ankle portions 14 and 12, and the upper and lower oblique surfaces 72 and 68, are oblique or oriented at an oblique angle $\Theta$. In one aspect, the attachment sections 22 and 38 can be oriented between approximately 20 and 70 degrees with respect to a horizontal axis. In another aspect, the attachment sections 22 and 38 can be oriented between approximately 30 and 60 degrees with respect to a horizontal axis. In another aspect, the attachment sections 22 and 38 can be oriented at approximately 45 degrees with respect to a horizontal axis, as shown. Thus, the upper forefoot portion 14 extends rearwardly and downwardly through the attachment section 22. The ankle portion 12 likewise extends downwardly and rearwardly through the attachment section 38.

The oblique angle of the attachment sections 22 and 38 allows the attachment sections 22 and 38 to extend a horizontal distance $L_h$ while having a longer length L. It will be appreciated that a horizontal attachment section, as shown in dashed lines, has a length $L_h$ that is relatively short compared to the length L of the attachment sections 22 and 38. In addition, the oblique angle of the attachment sections 22 and 38 allows the attachment sections 22 and 38 to have a longer length L while extending to vertical elevation E. It will be appreciated that a vertical attachment section, as shown in dashed lines, with the same length extends to a relatively higher vertical elevation $E_b$ than the relatively lower vertical elevation E of the attachment sections 22 and 38. Thus, the attachment sections 22 and 38 can provide a longer lever arm while having a shorter vertical elevation. Thus, the attachment sections 22 and 38 of the present invention extending at an oblique angle allows a longer length L without extending beyond a vertical elevation of a vertical attachment section of a J-shape. The longer attachment sections 22 and 38 provide a longer lever arm can increase the flexing or bending at the ankle section 26, and thus can improve the performance characteristics of the foot. The longer length of the forefoot portion allows extra length to store and return energy during use, contributes to extra spring or cushion of the foot, and improves vertical shock resistance.

Figure 2:
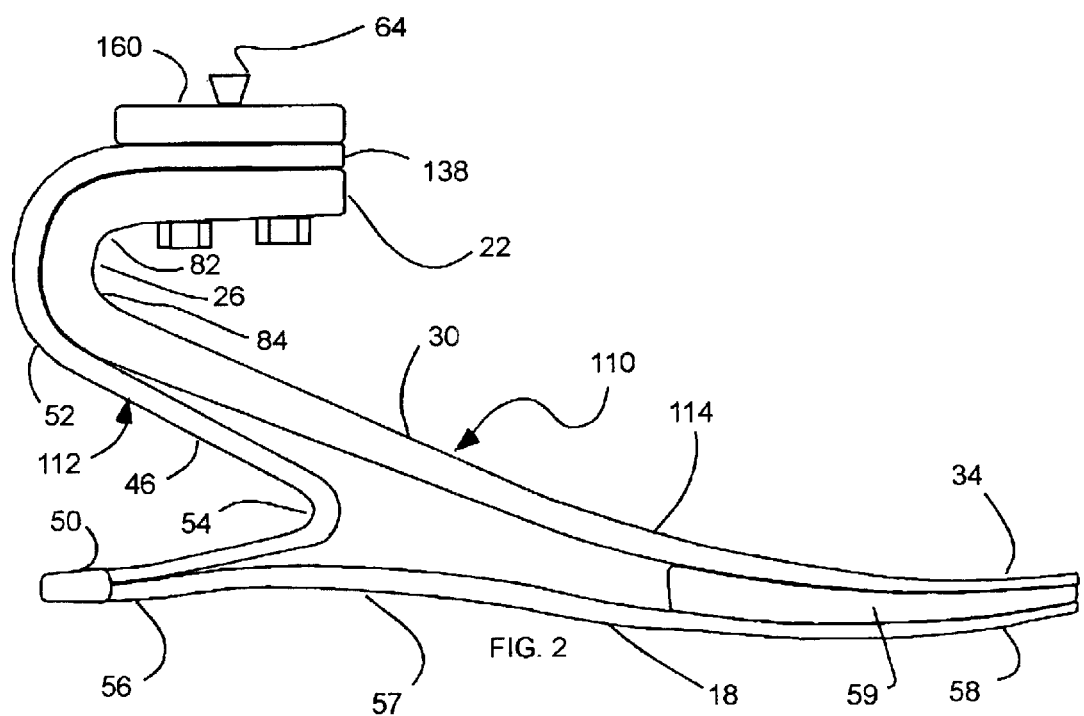
FIG. 2 is a side view of a prosthetic foot in accordance with an embodiment of the present invention.
Figure 3:
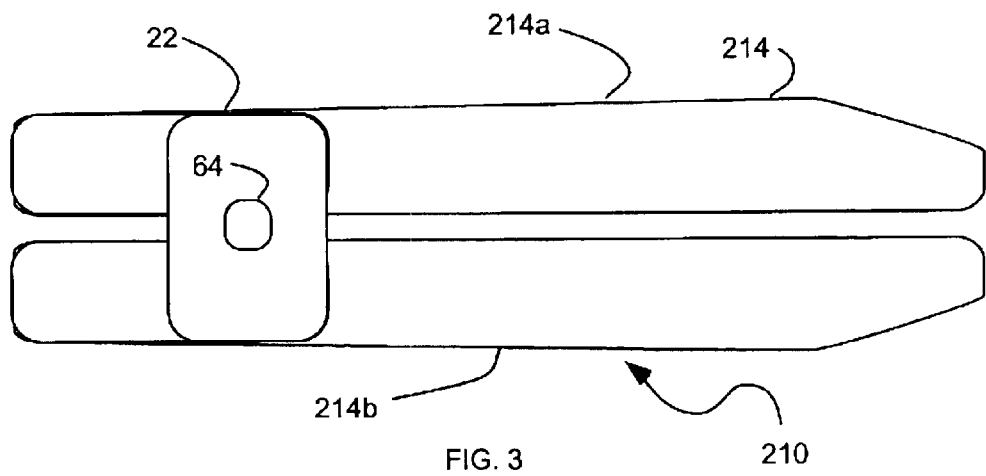
FIG. 3 is a top view of a prosthetic foot in accordance with an embodiment of the present invention.

In addition, the pyramid connector 64 can be moved fore or aft, or forward or rearward, to change the bending characteristics of the forefoot portion 14 or foot 10. In one aspect, the pyramid connector 64, or other connector, can be positioned at approximately the first third of the foot 10, with respect to, or measured from, the rearmost of the foot, as shown in FIGS. 1a and b. Alternatively, the connector can be positioned at approximately the first quarter, as shown in FIGS. 2 and 3. Positioning the connector at the first third provides a longer lever arm to store and return energy during use, contributes to extra spring or cushion of the foot, and improves vertical shock resistance.

The entire foot 10, or the upper forefoot portion 14 and lower footplate 18, can be an energy-storing member that flexes and bends under a load to store energy, and returns to its original configuration while the load is released to release the stored energy. The forefoot portion 14, the ankle portion 12 and the footplate 18 can include or be formed of a flexible and resilient material. For example, the material can be a composite with fibers disposed in a resin matrix. The fiber can be disposed in unidirectional, mat or weave with several layers. As the amputee steps, or pivots forward, on the prosthetic foot 10, the forefoot portion 14 and the lower footplate 18 deflect. Because the forefoot portion 14 and lower footplate 18 are made of a resilient material, the forefoot portion 14 and the lower footplate 18 act as a spring, and store the energy to be released as the user moves forward. Similarly, as the user steps on the footplate 18, the footplate and the ankle portion 12 deflect and store energy to be released as the amputee pivots forward.

The ankle sections 26 and 42 of the forefoot and ankle portions 14 and 12 each can include a discrete, straight section that is oriented substantially vertically. With respect to the forefoot portion 14 can include a first curved section 82 interconnecting the attachment section 22 and the ankle section 26. Similarly, a second curved section 84 can interconnect the ankle section 26 and the arch section 30. Thus, the ankle section 26 can include the discrete, straight section intermediate two curved sections 82 and 84. The forefoot portion 14 thus can extend 1) rearwardly and/or downwardly through the attachment section 22, 2) rearwardly and downwardly through the first curved section 82, 3) downwardly through the straight section or ankle section 26, 4) downwardly and forwardly through the second curved section 84, 5) forwardly and/or downwardly through the arch section 30, and 6) to the toe section 34. The discrete straight section of the ankle section 26 allows the forefoot portion 14 to be longer, and thus to store and return more energy during use, contribute to extra spring or cushion of the foot, and to improve vertical shock resistance.

In addition, the ankle section 26 of the forefoot portion 14 can be positioned at a rearmost location of the foot device 10, and over the heel section 46 of the lower footplate 18 or ankle portion 12. Thus, the forefoot portion 14 extends from the toe section 34 at the front of the foot, to above the heel section 46 at the rear of the foot. Thus, the forefoot portion 14 can be further elongated to store and return energy during use, to contribute to extra spring or cushion of the foot, and to improve vertical shock resistance.

The prosthetic foot 10 or ankle portion 12 also can include an energy transfer member 90 disposed between the heel section 54 of the ankle portion 12 and the ankle section 26 of the forefoot portion 14. The energy transfer member 90 can be positioned between the intermediate section 46 and the heel section 54 of the ankle portion 12. Thus, as the heel section 54 of the ankle portion 12 flexes or displaces during use, the energy transfer member 90 is compressed. The energy transfer member 90 can variably transfer energy from the heel section 54 of the ankle portion 12 to the foot, ranging from a small amount of energy during small deflections, to a large amount of energy during large deflections. The energy transfer member 90 can include a foam material. In addition, the energy transfer member 90 can include one or more such members, such as a permanent member 92 and a removable member 94. The permanent member 92 can be fixedly attached to the ankle portion 12, while the removable member 94 can be removably positioned. Thus, various different removable members 94, with various different stiffnesses, can be selectively positioned for use. The energy transfer members can form bumpers and can provide extra strength and extra stiffness for strenuous activities.

Referring to FIG. 2, another prosthetic foot 110 is shown that is similar in many respects to the foot described above. The foot 110 can include an upper forefoot portion 114, similar to that above, and an ankle portion 112. The attachment portions 122 and 138 of the forefoot and ankle portions 114 and 112 can be oriented horizontally. Similarly, the attachment member 160 can include a lower attachment surface that is also horizontal.

Referring to FIG. 3, another prosthetic foot 210 is shown that can be similar in many respects to those described above. The foot 210 can include an upper forefoot portion 214, a ankle portion 212, and a lower footplate 218, similar to those described above. The forefoot portion 214 can include two or more portions, such as first and second portions 214a and b, disposed adjacent one another in a side-by-side relationship. The two portions 214a and b can be laterally separated by a gap. The two portions allow the forefoot portion to mimic the toe rotation of a natural foot. The first and second portions 214a and b can be independently movable with respect to one another. Because the foot 10 includes the two portions, the foot 10 is able to respond to uneven terrain more like a natural foot with rotating toes. In addition, the foot 10 is better able to simulate toe and axial foot rotation. The forefoot portion can be split along substantially the entire length. The footplate or heel portion can be similarly split. It is of course understood that the forefoot portion, footplate, and/or heel portion can be partially or wholly split. The first and second portions can be mirror images of one another, or can be configured to resemble an actual foot. In addition, the first and second portions can have different spring forces, or stiffness, to better simulate a natural foot. The ankle portion 212 and the lower footplate 218 can be similarly split.

Referring to FIG. 4, another prosthetic foot 310 is shown that is similar in many respects to the prosthetic feet described above. The foot 310 can include a forefoot portion 314 that extends only through the arch section 30.

Referring to FIG. 5, another prosthetic foot 410 is shown that is similar in many respects to the prosthetic feet described above. The foot 410 can include a lower footplate 18 attached to the upper forefoot portion 114, as opposed to the ankle portion as shown in FIGS. 1a and 2. The lower footplate 18 can have a toe section 58 attached to the toe section 34 of the upper forefoot portion 114. The footplate 18 can extend rearwardly through the arch 57 to the heel section 56. The attachment of the lower footplate 18 to the forefoot portion 12 can form the primary or only attachment of the footplate 18 to the prosthetic foot 10. The attachment can be formed by wrapping the toe sections 34 and 58 with fibers in a resin matrix. A gap can be formed between the heel section 56 of the lower footplate 18 and the heel section 50 of the ankle portion 112 so that the heel sections 50 and 56 are not positively or directly attached. A cushion member can be disposed between the heel sections.

Referring to FIG. 6, another prosthetic foot 510 is shown that is similar in many respects to the prosthetic feet described above. The foot 510 includes only a forefoot portion 114 and a heel portion 112, without a footplate as described above. In addition, the prosthetic foot 510 can include an ankle reinforcement member 514 to reinforce the ankle portion 112, and to provide extra strength and/or extra stiffness for strenuous activities. The ankle reinforcement member 514 can be disposed adjacent or proximate to the ankle portion 112. The ankle reinforcement member can include an attachment section attached to the attachment member 160, and can extend to a heel section 518 spaced apart from and above the heel section 50 of the ankle portion 112. Thus, during extreme use or deflection of the ankle portion 112, the ankle reinforcement member 514 is engaged. An energy transfer member 524 can be disposed between the heel sections 518 and 50. Various different members 524 with varying stiffnesses can be provided to selectively alter the strength and/or stiffness of the foot. The stiffness or strength of the ankle portion 112, and the ankle reinforcement member 514 can be configured so that the heel section 50 of the ankle portion 112 contacts or engages the heel section 518 of the ankle reinforcement member based on the user's body weight, such as at 1 gravity.

Various aspects of such energy-storing prosthetic feet are shown and described in U.S. Pat. Nos. 5,944,760; 6,197,068; and 6,241,776, which are herein incorporated by reference.

It is to be understood that the above-referenced arrangements are only illustrative of the application for the principles of the present invention. Numerous modifications and alternative arrangements can be devised without departing from the spirit and scope of the present invention while the present invention has been shown in the drawings and fully described above with particularity and detail in connection with what is presently deemed to be the most practical and preferred embodiments(s) of the invention, it will be apparent to those of ordinary skill in the art that numerous modifications can be made without departing from the principles and concepts of the invention as set forth in the claims.

What is claimed is:

1. A prosthetic foot device, comprising:
   a) an elongated forefoot portion extending 1) rearwardly through an upper attachment section configured to be coupled to a limb of an amputee, 2) downwardly through an ankle section positioned at an ankle location of a natural foot, 3) forwardly through an arch section, and 4) to a toe section positioned at a toe location of a natural foot; and
   b) an elongated rear ankle portion extending 1) rearwardly through an upper attachment section attached to the attachment section of the forefoot portion, 2) downwardly through an ankle section, 3) forwardly under the ankle section of the forefoot portion, and 4) rearwardly to a heel section positioned at a heel location of a natural heel.

2. A device in accordance with claim 1, wherein the forefoot portion and the ankle portion are flexible to store energy and resilient to return energy.

3. A device in accordance with claim 2, wherein the forefoot portion and the ankle portion include a composite material with fiber in a resin matrix.

4. A device in accordance with claim 1, further comprising:
   a lower footplate, attached to the ankle portion, and extending forwardly 1) through a heel section attached to the heel section of the ankle portion, 2) an arch section, and 3) to a toe section positioned at a toe location of a natural foot.

5. A device in accordance with claim 4, further comprising a cushion member disposed between the toe section of the forefoot portion and the toe section of the lower footplate.

6. A device in accordance with claim 1, further comprising:
   a lower footplate, attached to the forefoot portion, and extending rearwardly 1) through a toe section attached to the toe section of the forefoot portion, 2) an arch section, and 3) to a heel section positioned at a heel location of a natural foot.

7. A device in accordance with claim 1, wherein the ankle portion has a substantially s-shaped profile.

8. A device in accordance with claim 1, wherein the forefoot portion includes at least two laterally separated and adjacent forefoot portions.

9. A device in accordance with claim 1, wherein the upper attachment section of the upper forefoot portion and the upper attachment section of the ankle portion are disposed at an oblique angle.

10. A device in accordance with claim 9, further comprising:
    an attachment member, configured to be coupled to a limb of an amputee, having a lower oblique surface; and
    wherein the upper attachment section of the forefoot portion and the upper attachment section of the ankle portion are attached to the lower oblique surface of the attachment member.

11. A device in accordance with claim 1, wherein:
    the ankle section of the forefoot portion includes a discrete, straight section oriented substantially vertically; and
    the forefoot portion further includes a first curved section interconnecting the attachment section and the straight section, and a second curved section interconnecting the straight section and the arch section.

12. A device in accordance with claim 1, further comprising:
    at least one energy transfer member, disposed between the heel section and the ankle section of the rear ankle portion, to transfer energy from the heel section of the ankle portion to the ankle section of the ankle portion during use.

13. A device in accordance with claim 1, further comprising:

a reinforcement member having an attachment section attached to the rear ankle portion and a heel section positioned above the heel section of the ankle portion.

14. A prosthetic foot device, comprising:

a) an attachment member, couplable to a limb of an amputee;

b) an elongated, upper forefoot, attached to the attachment member, extending 1) rearwardly through an upper attachment section attached to the attachment member, 2) downwardly through an ankle section positioned at an ankle location of a natural foot, and 3) forwardly to a toe section positioned at a toe location of a natural foot;

c) an elongated ankle portion, attached to the attachment member, extending 1) rearwardly through an upper attachment section attached to the attachment member, 2) downwardly through an ankle section, 3) forwardly under the ankle section of the upper forefoot, and 4) rearwardly to a heel section positioned at a heel location of a natural heel; and d) an ankle reinforcement member, attached to the attachment member and disposed proximate to the ankle portion, extending 1) rearwardly through an upper attachment section attached to the attachment member, 2) downwardly through an ankle section, 3) forwardly under the ankle section of the upper forefoot, and 4) rearwardly to a position above the heel section of the ankle portion.

15. A device in accordance with claim 14, wherein the forefoot portion defines a spring that flexes under a load to store energy, and returns to an original configuration while the load is released to release the stored energy; and wherein the ankle portion and the ankle reinforcement member define resilient spring members that flex under a load to absorb shock.

16. A device in accordance with claim 14, wherein the ankle portion and the ankle reinforcement member each has a substantially s-shaped profile.

17. A device in accordance with claim 14, wherein:

the ankle section of the forefoot includes a discrete, straight section oriented substantially vertically; and the forefoot portion further includes a first curved section interconnecting the attachment section of the forefoot and the straight section, and a second curved section interconnecting the straight section and the toe section.

* * * * *